United States Patent [19]
Furlong

[11] Patent Number: 5,672,515
[45] Date of Patent: Sep. 30, 1997

[54] SIMULTANEOUS DUAL EXCITATION/ SINGLE EMISSION FLUORESCENT SENSING METHOD FOR PH AND $PCO_2$

[75] Inventor: Steven C. Furlong, Maple Grove, Minn.

[73] Assignee: Optical Sensors Incorporated, Minneapolis, Minn.

[21] Appl. No.: 526,950

[22] Filed: Sep. 12, 1995

[51] Int. Cl.[6] .................................................. G01N 21/64
[52] U.S. Cl. ........................ 436/133; 436/163; 436/172; 422/82.08
[58] Field of Search ............... 422/82.06, 82.07, 422/82.08; 436/172, 133, 163; 250/227.21, 458.1, 459.1

[56] References Cited

U.S. PATENT DOCUMENTS

| | | |
|---|---|---|
| 4,548,907 | 10/1985 | Seitz et al. . |
| 4,792,689 | 12/1988 | Peterson . |
| 5,094,958 | 3/1992 | Klainer et al. . |
| 5,102,625 | 4/1992 | Milo ............................ 422/82.07 |
| 5,114,864 | 5/1992 | Walt . |
| 5,307,146 | 4/1994 | Porter et al. . |
| 5,315,993 | 5/1994 | Alcala ............................ 128/634 |
| 5,383,023 | 1/1995 | Walleczek ......................... 356/417 |

*Primary Examiner*—Jeffrey Snay
*Attorney, Agent, or Firm*—Reed & Associates

[57] ABSTRACT

A simultaneous dual excitation/single emission ratiometric method using fiber optic sensors is provided for detecting or measuring a parameter of interest in a sample, including pH, concentration of gases such as $CO_2$, and the like. The method involves simultaneously providing modulated optical light corresponding to first and second regions of an indicator species' absorption or excitation spectrum, detecting modulated emission signals from the indicator species, demodulating the emission signals, calculating the apparent quantity of analyte present in the sample from the indicator emission signals and correcting the apparent quantity of analyte present for variations resulting from external factors, by determining the ratio of the demodulated indicator emission signals. An apparatus is provided for performing the method as well.

29 Claims, 3 Drawing Sheets

SIMULTANEOUS DUAL EXCITATION/ SINGLE EMISSION FLUORESCENT SENSING METHOD FOR PH AND $PCO_2$

TECHNICAL FIELD

The present invention relates generally to methods of using optical sensors for measuring analytes in a sample. More particularly, the invention relates to a novel ratiometric method of measuring an analyte in a sample. The method is useful, inter alia, for the measurement of pH and detection and quantitation of gases such as carbon dioxide.

BACKGROUND

Chemical sensors are generally known for use in a wide variety of areas such as medicine, scientific research, industrial applications and the like. Fiber optic and electrochemical approaches are generally known for use in situations where it is desired to detect and/or measure the concentration of a parameter at a remote location without requiring electrical communication with the remote location. Structures, properties, functions and operational details of fiber optic chemical sensors can be found in U.S. Pat. No. 4,577,109 to Hirschfeld, U.S. Pat. No. 4,785,814 to Kane, and U.S. Pat. No. 4,842,783 to Blaylock, as well as Seitz, "Chemical Sensors Based on Fiber Optics," *Analytical Chemistry*, Vol. 56, No. 1, January 1984, and Wolfbeis, *Fiber Optic Chemical Sensors and Biosensors*, Volumes I and II, CRC Press, Boca Raton, Fla., 1991, each of which is incorporated by reference herein.

Publications such as these generally illustrate that is it known to integrate a chemical sensor with a fiber optic waveguide, an electrochemical gas sensor or the like, in a manner such that the chemical sensor will interact with the analyte. This interaction results in a change in optical properties, which change is probed and detected through the fiber optic waveguide or the like. These optical properties of chemical sensor compositions typically involve changes in colors or in color intensities. In these types of systems, it is possible to detect particularly minute changes in the parameter or parameters being monitored in order to thereby provide especially sensitive remote monitoring capabilities.

Chemical sensor compositions that are incorporated at the distal end of fiber optic sensors are often configured as membranes that are secured at the distal tip end of the waveguide device or optrode. Sensors of this general type are useful in measuring gas concentrations such as carbon dioxide and oxygen, monitoring the pH of a fluid, and the like. Ion concentrations can also be detected, such as potassium, sodium, calcium and metal ions.

A typical fiber optic sensor device positions the sensor material at a generally distal location with the assistance of one or more types of support means. Support means must be such as to permit interaction between the parameter-sensitive indicator, e.g., a fluorescent dye or the like, and the substance being subjected to monitoring, measurement and/ or detection. Known approaches in this regard include the use of permeable membranes and composites incorporating micro-encapsulation.

One problem with such intensity-based fiber optic chemical sensors is that they are sensitive to interfering effects such as temperature changes, mechanical stresses applied to the fiber, vibration-induced misalignment of optical components, and the like. These physical effects induce unwanted intensity fluctuations in the output signal not related to changes in the quantity of the analyte and result in measurement errors.

A well-recognized problem with commonly used parameter-sensitive chemical indicators is that they are photolabile. The radiant energy in light induces photochemical reactions which hasten the decomposition of the indicators and thereby abbreviate their useful lives. This photodecomposition results in a coordinate signal decay commonly referred to as photodrift, or simply drift.

Various approaches have been used to solve the problem of photodrift. For example, some parameter-sensitive indicators have visible spectrum with a portion that is sensitive to environmental changes and a portion that shows either a total environmental insensitivity (e.g., an isosbestic point) or a relative insensitivity. This spectral property can be used to advantage to compensate for photodrift by ratioing the signal from the environmentally sensitive portion of a indicator's spectrum to that from the insensitive portion of the spectrum. The ratio of the signals should be invariant as the indicator molecule photodecomposes and the absolute signal value decays. This principle has been employed to ratio the signals obtained from a fluorescent indicator when measuring pH. Wolfbeis, supra, Vol. I, p. 103.

Another strategy for contending with the problem of photodrift involves the incorporation of a separate internal reference dye in the sensor. The reference indicator is chosen to be environmentally insensitive and to photodecompose at the same rate as the parameter-sensitive indicator. When an internal reference dye is incorporated into an optical sensor, the signal from the environmentally sensitive indicator may be calibrated by comparison with the signal from the reference dye. As a result of the similarity of the decay rates of the indicator dye and the reference dye, the ratio of the signals should be invariant as the two dyes photodecompose.

In addition to the problem of photodrift, photochemical reactions that are the result of exposure to light ultimately engender the decomposition of the organic dyes used as chemical indicators. As an indicator decomposes, with a concomitant decrease in signal intensity, the sensor must be repeatedly calibrated. The use of a system employing a method of ratioing signals from indicator and reference dyes not only permits compensation for photodrift but extends the intervals between which the sensor needs to be recalibrated to operate with accuracy and precision as well.

Calibration of the emission signal of the indicator dye may be effected by ratioing it to that of the reference dye. Thus, the indicator and reference dyes may be irradiated with light of a specific wavelength, more than one specific wavelength, or a range of wavelengths, which may or may not be the wavelength of maximum absorption. The fluorescence emission may be measured at specific wavelengths, which may or may not be the wavelength of maximum emission intensity, or a range of wavelengths in conjunction with specific light filtering devices. By this procedure, the fluorescence emission of the indicator dye may be discerned from that of the reference dye. Expressing the emission of the indicator dye as a fraction of the emission of the reference dye yields a signal ratio that is sensitive to the analyte of interest and less sensitive to the effects of exposure to light (photodecomposition of the signal, photodecomposition of the compound) than a single indicator dye sensor composition, and a prolonged useful life of the sensor.

U.S. Pat. No. 4,792,689 to Peterson describes an improved fiber optic sensor and a method for correcting for variations in signal intensity in fiber optic sensors. This approach, typically referred to as "single excitation/dual emission" uses a fiber optic sensor having two fluorescent indicator dyes, one sensitive and one insensitive to the analyte of interest. Two wavelengths of light are passed through a single fiber optic sensor, thereby exciting the sensitive and insensitive dyes, one of which produces an analyte-sensitive fluorescence emission and the other of which produces an analyte insensitive emission. The dyes are chosen to simultaneously fluoresce at different optical wavelengths; these fluorescent emission signals are carried to the detection electro-optics by a single fiber optic waveguide. In this "common mode" method, all of the physical phenomena presented occur simultaneously and traverse the same optical pathway—both for the delivery of optical energy to the sensing region and for the capture of the resultant fluorescent signals.

At this point in his teachings Peterson interjects a dispersive optical element, i.e., a dichroic mirror, which spatially separates the sensing and reference optical signals. Each of these signals is routed to its respective, separate detector circuitry, i.e., the common-mode optical pathway has been interrupted at the last possible moment. Ideally, the two signals would have been routed simultaneously to the same optical detection circuitry and independently detected. In this manner, all common-mode effects, even changes in the electronic gain of the detector circuitry, would have been corrected for by ratioing the sensing and reference signals.

Improvements on the Peterson method have been described for "simultaneous common-mode" sensing techniques of fiber optic chemical sensing. For example, the so-called "time decay" method is a "single excitation/single emission" method in which a single fluorescent (or phosphorescent) dye species is used to sense the presence of dissolved oxygen. Typically, the emission signal is captured in the time domain by a high speed analog-to-digital converter and direct analysis (normally the determination of the 1/e decay time) of the signal yields the oxygen concentration. The results are independent of the absolute intensity of the returning optical signal. Although this technique is conceptually compelling because no reference dye is needed, it has not been readily commercializable for a variety of reasons, nor can it be used in the area of pH sensing.

Other methods of correcting common-mode effects include two general methods referred to as "dual excitation/ dual emission ratiometric sensing" and "dual excitation/ single emission sensing."

In the dual excitation/dual emission method, two dye species are used in the sensing region of a fiber optic sensor in a manner similar to that described by Peterson. In contrast to Peterson, the dye species have different absorption regions and they fluoresce into different optical spectra. As with the Peterson method, dual excitation/dual emission systems separate the signals prior to detection and they have separate optical detectors. Thus, the common-mode optical pathway is disrupted, thereby introducing noncommon-mode effects.

In a typical dual excitation/single emission system, a single dye species is used which absorbs optical energy at two different excitation wavelengths and emits optical energy into the same spectral region. This system has the advantage that, since the resultant emission signal is the same color for both excitation signals, the identical optical pathway, i.e., the same optical filters and detector system, can be used for both signals. However, in this system, the only way to distinguish the two signals is to make the measurements at different times; simultaneity is lost in the reference measurement. Thus, for example, if the instrument or optical energy source drifts between the sensing and reference measurements, the ratio has been corrupted.

Thus, there is a need in the art for a method which provides for simultaneous dual excitation/single emission sensing of analytes which corrects for all common-mode effects by ratioing sensing and reference emission signals from an environment-sensitive indicator species.

SUMMARY OF THE INVENTION

Accordingly, it is a primary object of the invention to address the above-mentioned needs in the art by providing a novel ratiometric method of quantitating an analyte in a sample.

It is another object of the invention to address these needs by providing a novel method for quantitating an analyte in a sample that involves the use of a dual excitation/single emission ratiometric technique.

It is another object of the invention to provide an apparatus for quantitating an analyte in a sample that incorporates a dual excitation/single emission method.

Additional objects, advantages and novel features of the invention will be set forth in part in the description which follows, and in part will become apparent to those skilled in the art upon examination of the following, or may be learned by practice of the invention.

In one aspect of the invention, a method for quantitating an analyte in a sample is provided that involves providing an optical sensor having an indicator species having an absorption or excitation spectrum that includes a first region and a second region such that the first and second regions do not overlap substantially, and an emission spectrum that is distinct from the absorption or excitation spectrum, contacting the sample with the optical sensor, simultaneously exciting the indicator species using radiation of a first optical wavelength corresponding to the first region, thereby producing a first indicator emission signal, and radiation of a second optical wavelength corresponding to the second region, thereby producing a second indicator emission signal, wherein the radiation of first and second optical wavelengths are respectively transmitted at first and second electrical frequencies, calculating the apparent quantity of analyte present in the sample from the first and second indicator emission signals, and correcting the apparent quantity of analyte present for variations resulting from external factors, by determining the ratio of the first and second indicator emission signals.

In another aspect of the invention, an apparatus is provided that includes an optical sensor having an indicator species with an absorption or excitation spectrum that includes a first region and a second region such that the first and second regions do not overlap substantially, and an emission spectrum that is distinct from the absorption or excitation spectrum, a means for simultaneously generating radiation of first and second optical wavelengths by which the indicator species can be excited, a means for modulating the first and second optical signals, a means to detect the emission signals from the excited indicator and a means to demodulate simultaneously the emission signals.

BRIEF DESCRIPTION OF THE FIGURES

In the course of this description, reference will be made to the attached drawing, wherein.

DETAILED DESCRIPTION OF THE INVENTION

Figure 1:
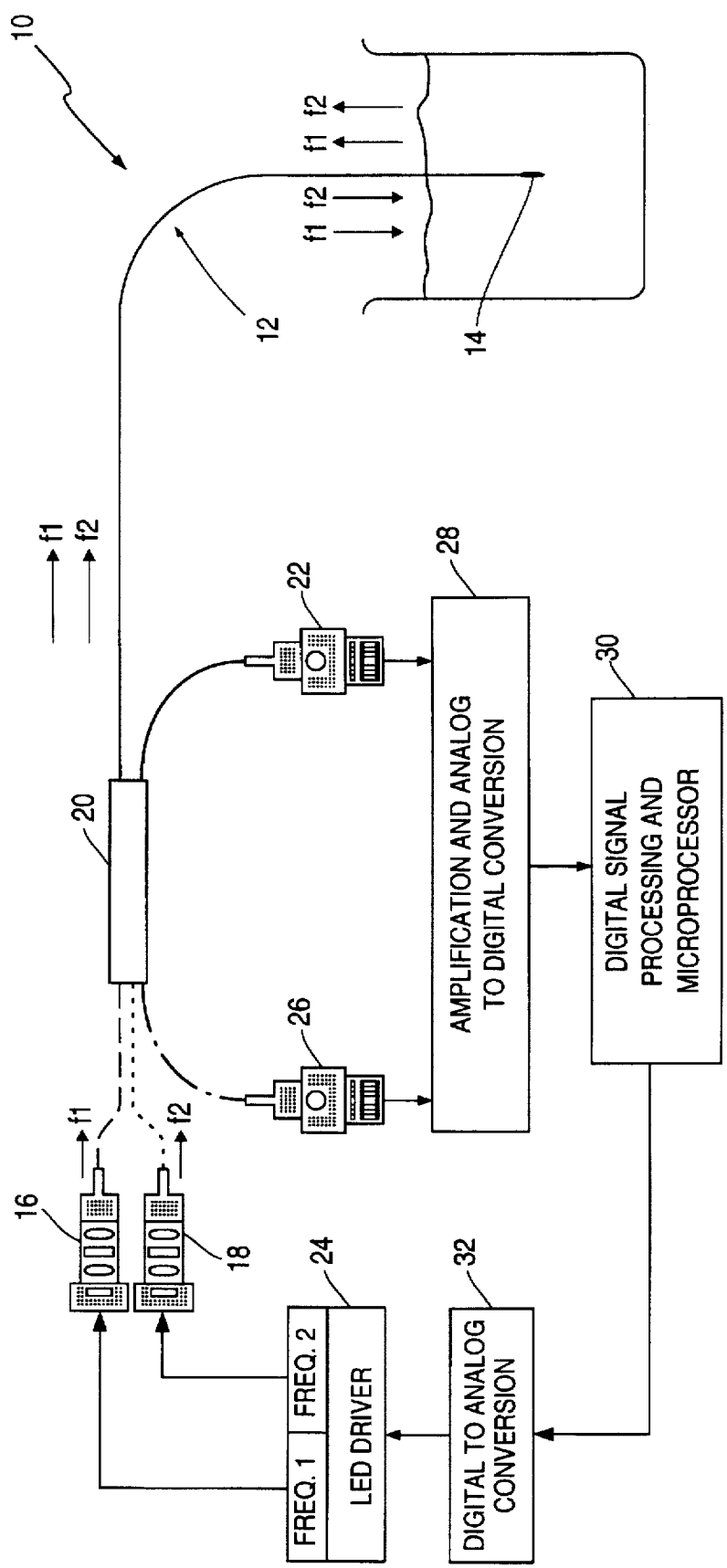
FIG. 1 is a schematic drawing of a system for quantitating an analyte in a sample that involves the use of a simultaneous dual excitation/single emission technique in accordance with the teachings of the invention.

Before the present apparatus and methods for quantitating an analyte in a sample are disclosed and described, it is to be understood that this invention is not limited to specific sensor formats, specific indicator compositions, or specific excitation energy sources as such, of course, may vary. It is also to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise. Thus, for example, reference to "source of excitation energy" or includes more than one source of excitation energy, reference to "an indicator material" includes mixtures of suitable indicator materials, reference to "an optical sensor" two or more such sensors, and the like.

In describing and claiming the present invention, the following terminology will be used in accordance with the definitions set out below.

The term "optical fiber means" is used herein to refer to a single optical fiber or a bundle of optical fibers. Suitable materials for optical fibers will be outlined below.

The term "sample" as used herein refers to a liquid or gaseous material which may be analyzed using the presently disclosed sensors, either with respect to a parameter such as pH, or with regard to the presence or concentration of gases such as carbon dioxide, or the like. Generally, "sample fluids" analyzed using the sensors manufactured herein will be physiological fluids such as blood.

The term "indicator" as in "indicator composition," "indicator material" or "indicator component" refers to a species which has an optical absorption or excitation spectrum that includes a first region that is sensitive to the analyte of interest in the sample undergoing analysis and a second region that is insensitive to the analyte. Preferably, the first and second regions do not overlap substantially. By the phrase "do not overlap substantially" is intended that the wavelength of peak sensitivity to the analyte of interest of the first region is separated by preferably more than 20 nanometers from the wavelength of maximum insensitivity to the analyte of the second region. In addition, the indicator species has an emission spectrum that is distinct from the absorption or excitation spectrum and emits in a third spectral region. The term "distinct" is used herein to signify that the indicator species has an emission spectrum that has a peak wavelength that is separated preferably by more than 25 nanometers from both the peak Of the first region and the most insensitive point of the second region.

For measuring pH, the indicator will generally be a fluorescent dye or some other fluorescent material which is pH-sensitive. For carbon dioxide sensors, virtually any pH-sensitive fluorescent or absorbent dye can be used, although preferred indicators include fluorescein and fluorescein derivatives such as carboxyfluorescein, seminaphthorhodafluor, seminaphthofluorescein, naphthofluorescein, hydroxypyrene trisulfonic acid, dichlorofluorescein and the like. Particularly preferred indicators are 8-hydroxypyrene-1,3,6-trisulfonic acid ("HPTS") and fluorescein.

The term "isosbestic point" is used herein to indicate a wavelength in the excitation or absorption spectrum of an indicator material that is insensitive to the changes in the analyte, to which the indicator material is sensitive at other optical wavelengths, i.e., the emission signal from the indicator species when exposed to incident light at the isosbestic point does not change with changing analyte concentration. Thus, for example, when an indicator compound exists in two distinct species, the interaction of an analyte in a sample with the indicator compound may lead to the conversion of one indicator species into the other. As this occurs, the excitation, absorption or emission spectrum can change such that one band of the spectrum may display an increase in amplitude with increased analyte concentration, while the amplitude of another band may simultaneously decay. Certain bands of the spectrum may be observed for which the amplitude does not change in response to changing concentrations of the analyte. Such analyte-insensitive regions of the spectrum are referred to herein as isosbestic points.

The invention, together with additional features and advantages thereof, may be best understood by reference to the following description taken in connection with the illustrative drawings.

With reference to FIG. 1 a system (10) is generally provided for quantitating an analyte, for example, $pCO_2$ or pH in a sample. The system comprises optical fiber means (12) that includes fluorescent dye species (14) having a first region of its absorption and/or excitation spectra which is analyte sensitive and a second region of its absorption and/or excitation spectra which is analyte insensitive. In response to light corresponding to the first region from first light source (16), e.g., blue light, and to the second region from second light source (18), e.g., violet light, the dye species emits light energy, e.g., fluoresces, into the same third spectral region, e.g., green light. An optional optical coupler (20) provides a means for combining the output of light source (16) and light source (18) to simultaneously excite dye species (14) at two distinct regions of its absorption or excitation spectrum. In addition, optical coupler (20) provides a means whereby a reference signal may be routed to reference detector (22). As shown in FIG. 1, light sources (16) and (18) are light emitting diodes.

At the outset, an optical fiber means is provided which serves to communicate optical signals from a sample fluid to a detection means. The optical fiber means will typically comprise a single elongated optical fiber, although it may comprise a bundle of optical fibers associated in parallel.

Examples of suitable fiber substrate materials include glass, plastic, glass/glass composite and glass/plastic composite fiber waveguides. A critical characteristic of optical fibers is attenuation of the optical signal. Thus, glasses which contain unacceptable levels of transition-metal impurities when prepared from naturally occurring materials lead to high absorption losses. Silica fibers of acceptable quality can be prepared from purified starting materials (e.g., silicon tetrachloride and germanium tetrachloride) using conventional glass-melting techniques and drawing into fibers.

Generally, although not necessarily, the fiber will be provided with a cladding means. As will be appreciated by those skilled in the art, the cladding means serves to provide structural support for an otherwise fragile fiber, and also provides a coating which guides light conducted along the fiber. In the present case, the cladding means typically comprises a fluoropolymer such as polymeric fluoroacrylate. However, the cladding means may also be comprised of glass, or it may comprise polystyrene, polyimide or any other suitable plastic material.

Preferably, the indicator species is a single fluorescent or phosphorescent dye species having an isosbestic point that can serve as the second region of the excitation or absorption spectrum. Alternatively, for an indicator species that can exist simultaneously in two forms, e.g., acid and base, the relative amounts of which depend on the presence of an analyte. The excitation and emission wavelengths used will then depend on the excitation or absorption spectra of the two forms of the dye species. For example, the acid and base forms of a pH-sensitive dye species can be excited simultaneously at independently modulated and distinct wavelengths and the intensity of the emission can be measured at the same optical wavelength for both excitations, demodulated and processed to obtain a ratiometric determination of the pH of the sample.

Indicator species may be provided on the distal tip of the optical fiber means by any method known in the art. One example of such a method is found in U.S. Pat. No. RE 31,879 to Lübbers et al. which discloses a device wherein indicator material is provided in solution form and separated from the external environment by a membrane. An alternative approach is to attach an indicator composition to the tip of an optical fiber using a silanization technique as described in, for example, U.S. Pat. No. 5,354,825 to Klainer et al. Still another technique involves direct bonding of photoactive polymers to the tip of an optical fiber, as described in U.S. Pat. No. 5,354,825 to Klainer et al. Still another approach involving the use of an inner adhesive layer for affixing an indicator composition to the distal end of a fiber optic sensor is disclosed in commonly assigned U.S. patent application Ser. No. 08/524,592, entitled "Method for Manufacturing Fiber Optic Sensors and Novel Sensors Provided Thereby," inventors Lynch et al., filed on Sep. 7, 1995.

Briefly, this method involves the deposition of a layer of a curable adhesive composition to the tip of an optical fiber using a simple dip coating procedure, partially or fully curing the adhesive layer so provided using moisture, heat, ultraviolet radiation or the like, coating the adhesive layer with at least one outer layer of a curable indicator-containing composition using a similar dip coating technique used to provide the adhesive layer and curing the outer layer. The coated probe tip is stored in a saline solution in order to hydrate the fiber coating.

Yet another approach involving the use of a $CO_2$-permeable end cap filled with a fluorescent indicator and affixed to the distal tip of the optical fiber means is disclosed in commonly assigned U.S. patent application Ser. No. 08/535,878, entitled "Optical Carbon Dioxide Sensor, and Associated Methods of Manufacture and Use" inventors Alderete et al., filed on Sep. 28, 1995.

Briefly, this method involves prefilling a $CO_2$-permeable silicone cap with a liquid solution containing a $CO_2$ sensing dye. The prefilled cap is applied over the tip of a fiber optic waveguide and secured using a silicone adhesive that is deposited onto the cap-fiber interface to secure the cap to the fiber. The capped fiber is then suspended in a humid environment to moisture-cure the silicone.

The source of light may be an incandescent lamp, an arc or flash lamp, a solid state emitter, or a laser. Preferably, the source of light is a light emitting diode ("LED").

The output of light sources (16) and (18) are simultaneously and independently amplitude modulated by electronic means. As depicted in FIG. 1, the output of light sources (16) and (18) are amplitude modulated at different electronic frequencies, $f_1$ and $f_2$ (indicated respectively by the dashed ( - - - - ) and dotted ( · · · · ) lines in FIG. 1), by light source driver (24), which is exemplified in FIG. 1 as an LED driver. The electronic frequencies are selected such that they can be electronically resolved. It is preferred that they differ by at least 1 Hz and that they are not multiples of each other, e.g., harmonics, or linear combinations thereof. It is also preferred that the electronic frequencies are not 60 Hz or multiples thereof.

Electronic modulation may be accomplished using amplitude modulation schemes, at a constant frequency, using current modulation (sinusoidal, triangular, square-wave or the like), voltage modulation or spatial filtering with optical shutters. Alternatively, electronic modulation using frequency modulation schemes, at constant amplitude, may be accomplished using methods well known in the art including acousto-optic modulation, electro-optic modulation or nonlinear crystals. In addition, the optical signals from light sources (16) and (18) may be modulated using phase modulation schemes, such as electro-optical modulation typically employing piezoelectric crystals. Frequency modulation and phase modulation may be useful in conjunction with coherent light sources while amplitude modulation schemes may be used with coherent and/or incoherent light sources. In one preferred embodiment, the optical signals from light sources (16) and (18) are modulated using amplitude modulation schemes, more particularly amplitude modulation schemes employing current modulation. The system may optionally include a means to generate a lamp reference signal which may be an optical coupler/beam splitter, the signal from which is routed to an optional reference detector.

Electronic modulation of the optical 'signals from light sources (16) and (18) results in the total returning emission signal from dye species (14) being composed of two distinct fluorescent components—a component at electronic frequency $f_1$ (the sensing signal the amplitude of which is pH dependent) and a second component at electronic frequency $f_2$ (the reference signal the amplitude of which is pH insensitive). The two emission signals are routed through optical coupler (20) and are presented simultaneously to optical detector (26) (the total returning emission signal is represented in FIG. 1 by the line composed of alternating dots and dashes ( · - · - )).

The optical detector may be a solid state detector or an array of such detectors, non-solid state detectors, thermal detectors or the like. Examples of solid state detectors include silicon detectors and arrays thereof. Examples of non-solid state detectors include photomultiplier tubes ("PMTs"). Thermal detectors include thermopiles and bolometers.

The signal detected from dye species (14) by optical detector (26) can be demodulated using any of a variety of demodulation schemes well known in the art. The scheme that can be used to demodulate the signal depends on what scheme was used to modulate the optical signals from light sources (16) and (18).

Thus, for optical signals that have been modulated using amplitude modulation schemes, demodulation may be done by any method well known in the art, including digital demodulation or analog demodulation schemes. If the samples were frequency or phase modulated, the signal detected from dye species (14) can be demodulated by frequency or phase demodulation schemes, respectively.

Preferably, amplitude modulated optical signals from dye species (14) are received by optical detector (26), which typically provides an analog output, amplified, digitized by a high-speed analog-to-digital (A/D) converter (28) and routed to a digital signal processing (DSP) device (30). Here, spectral analysis is performed on the digitized version of the detector output by discrete fourier transform ("DFT") techniques well known in the art. The net result is the demodulation and separation of the two emission signals into their respective amplitudes—the pH-dependent sensing signal and its simultaneously demodulated reference signal. These numerical results are then available for subsequent post-detection processing to quantify the analyte.

The DSP device (30) also serves as a digital microprocessor which, through digital-to-analog converter (32), provides a signal to light source driver (24) to modulate the output of light sources (16) and (18).

This fiber-optic based fluorescent sensing technique for pH and/or $pCO_2$ has applications for the measurement of pH and quantitation of dissolved gases such as carbon dioxide in samples, e.g., for measuring pH and $pCO_2$ in aqueous samples. Given the general remote sensing architecture of the instrument/sensor electro-optics, the technique is adaptable to any application that might require the remote monitoring of an acid-base chemistry system.

In addition, the invention may be useful when incorporated in paracorporeal blood gas monitoring system such as disclosed in commonly-assigned U.S. patent application Ser. No. 08/379,332, entitled "In Situ Calibration System for Sensors Located in a Physiologic Line," inventor Kimball et al., filed on Jan. 27, 1995, and described in Martin et al. (1994) *Proc. Biomed. Fiber Optic Instrumentation* 2131:426–436, each of which is incorporated by reference herein.

Briefly, the system includes fiber optic sensors that are contained in a housing with standard luer lock adapters that attach into an arterial pressure line, allowing monitoring to occur "paracorporeally"; patient blood is moved into the line and housing, via care-giver draw, for discrete measurements and returned to the patient upon completion of the measurement.

It will be appreciated by those working in the art that sensors fabricated using the presently disclosed and claimed techniques may be used in a wide variety of contexts, including measurement of carbon dioxide or other gases, glucose determination, measurement of potassium ions, calcium ions, magnesium ions, and the like. Also, while the invention has primarily been described in conjunction with the measurement of analytes in blood, the sensors fabricated using the present method may be used to evaluate a wide range of parameters in any number of sample types.

Thus, it is to be understood that while the invention has been described in conjunction with preferred specific embodiments thereof, the foregoing description, as well as the examples which follow, are intended to illustrate and not limit the scope of the invention. Other aspects, advantages and modifications within the scope of the invention will be apparent to those skilled in the art to which the invention pertains.

EXAMPLE 1

Use of Simultaneous Dual Excitation/Single Emission Method to Measure pH and $pCO_2$ A paracorporeal fiber optic blood gas and pH monitoring system employing the simultaneous dual excitation/single emission technique and apparatus as shown in FIG. 1 was used to measure arterial $pCO_2$ and pH as described in Martin et al., supra.

Human clinical data obtained using the paracorporeal device were compared with assay values generated by standard laboratory pH/blood gas techniques and analyzers, e.g., a Radiometer Corporation Model ABL 500-#2 blood gas analyzer. The arterial samples were split so that pH and $pCO_2$ were measured by each technique using the same sample. All procedures involving human subjects were approved by the appropriate clinical site review committee.

The fiber optic sensors used in these experiments for measuring arterial blood pH were prepared containing fluorescein (Aldrich, Milwaukee, Wis.), while those sensors used for measuring $pCO_2$ were prepared containing 8-hydroxypyrene-1,3,6-trisulfonic acid, trisodium salt ("HPTS") (Molecular Probes, Eugene, Oreg.). The sample was alternately interrogated using the pH and $pCO_2$ sensors as follows.

The indicator species in the fiber optic pH sensor was simultaneously exposed to excitation light centered at 488 nm and 442 nm, with an emission signal from the indicator species monitored in the region 529.5 nm±15.5 nm. The 488 nm and 442 nm signals were respectively modulated at 37 Hz and 24 Hz. The 442 nm signal correspond to a pH-insensitive region of the fluorescein excitation spectrum. The optical signals were modulated using an amplitude modulation scheme using sinusoidal current modulation.

The indicator species in the fiber optic $pCO_2$ sensor was simultaneously exposed to excitation light centered at 442 nm and 415 nm, with an emission signal from the indicator species monitored in the region 529.5±15.5 nm. The 442 nm and 415 nm signals were respectively modulated at 37 Hz and 24 Hz. The 415 nm signal correspond to an isosbestic point of the HPTS excitation spectrum. The optical signals were modulated as describe above.

The emission signals were detected using a silicon detector, the analog output signal from which was digitized and fed to a microprocessor where the signals were demodulated.

Sensor precision, expressed as standard deviation about the mean ("SD"), and sensor accuracy, expressed as average difference from the values obtained using standard blood-gas analyzers were calculated using the data gathered from 10 independent patient blood-gas measurements.

In 10 measurements of arterial blood pH, the value obtained using the standard blood-gas analyzer was 7.414. The value obtained using the paracorporeal device employing the simultaneous dual excitation/single emission technique and apparatus of the invention was 7.375 (SD=0.008). The average difference between the ten values obtained using the standard analyzer and the paracorporeal method was 0.039.

The arterial $pCO_2$ value obtained using the standard blood-gas analyzer was 38.3 while that obtained using the paracorporeal device was 40.6 (SD=4.00%) while the average difference was 5.9%.

Figure 2:
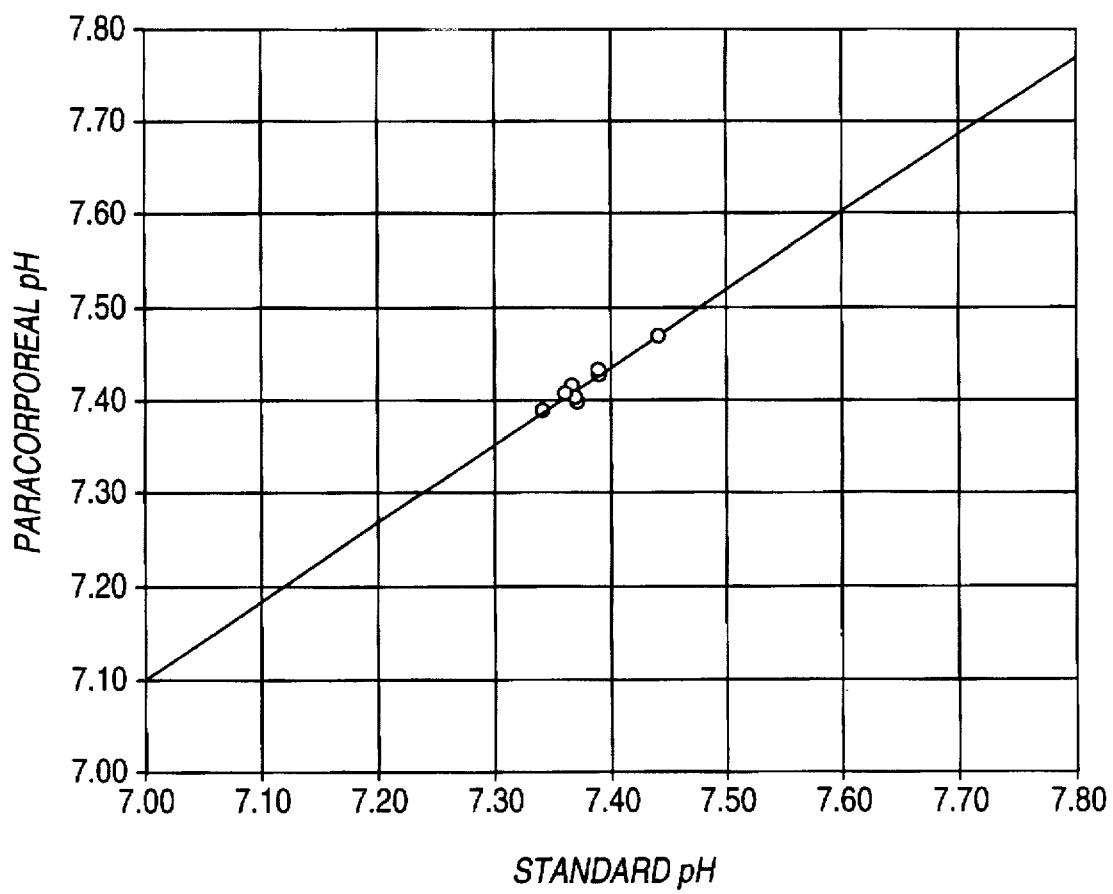
FIG. 2 is a graphical representation of a comparison of arterial blood pH obtained using a standard laboratory blood-gas analyzer with that obtained using a paracorporeal fiber optic sensor system and a simultaneous dual excitation/ single emission technique in accordance with the teachings of the invention.
Figure 3:
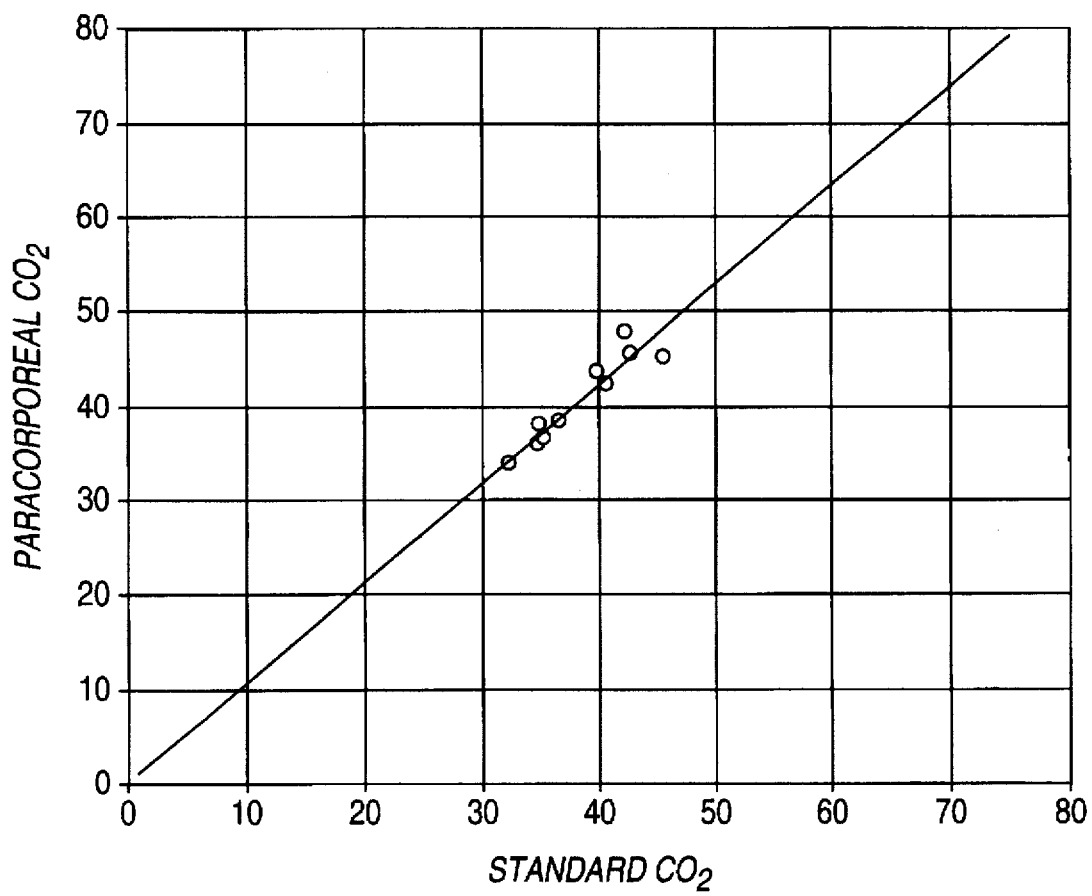
FIG. 3 is a graphical representation of a comparison of arterial blood $pCO_2$ obtained using a standard laboratory blood-gas analyzer with that obtained using a paracorporeal fiber optic sensor system and a simultaneous dual excitation/ single emission technique in accordance with the teachings of the invention.

Sensor performance was plotted for pH and $pCO_2$ in FIG. 2 and FIG. 3, respectively, which show individual data points for blood pH and $pCO_2$ measurements, respectively, as well as the identity lines calculated by linear regression analysis (pH: $r^2=0.906$; $pCO_2$: $r^2=0.884$).

These data demonstrate the accuracy and precision of data collected from fiber optic sensors using the simultaneous dual excitation/single emission system of the of the invention.

We claim:

1. A method for quantitating an analyte in a sample, comprising:

(a) providing an optical sensor comprising an optical fiber means having a distal end portion for contacting the fluid sample, and a proximal end portion for communication with a means for receiving a signal from the distal end portion, and wherein the distal end portion has an analyte sensing means comprising an indicator species having an absorption or excitation spectrum that includes a first region and a second region and wherein the first and second regions do not overlap substantially, and an emission spectrum that is distinct from the absorption or excitation spectrum;

(b) contacting the sample with the distal end portion of the optical sensor;

(c) simultaneously exciting the indicator species using modulated radiation of a first optical wavelength corresponding to the first region, thereby producing a first modulated indicator emission signal, and modulated radiation of a second optical wavelength corresponding to the second region, thereby producing a second modulated indicator emission signal, wherein the radiation of first and second optical wavelengths are respectively transmitted at first and second electrical frequencies;

(d) demodulating the first and second modulated indicator emission signals;

(e) calculating the apparent quantity of analyte present in the sample from the first and second indicator emission signals; and (f) correcting the apparent quantity of analyte present for variations resulting from external factors, by determining the ratio of the first and second indicator emission signals.

2. The method of claim 1, wherein the sample is a fluid sample.

3. The method of claim 1, wherein the analyte sensing means comprises an indicator species having an excitation spectrum that includes a first region and a second region.

4. The method of claim 1, wherein the analyte sensing means comprises an indicator species having an absorption spectrum that includes a first region and a second region.

5. The method of claim 1, wherein the first and second regions respectively correspond to the acid and base forms of the indicator species.

6. The method of claim 3, wherein the first and second regions respectively correspond to the acid and base forms of the indicator species.

7. The method of claim 3, wherein the first region of the excitation spectrum is sensitive to the analyte and the second region of the excitation spectrum is insensitive to the analyte.

8. The method of claim 7, wherein the second region is the isosbestic point.

9. The method of claim 1, wherein the analyte is selected from the group consisting of pH and $pCO_2$.

10. The method of claim 9, wherein the analyte is pH.

11. The method of claim 9, wherein the analyte is $pCO_2$.

12. The method of claim 1, wherein the indicator species is selected from the group consisting of fluorescein, carboxyfluorescein, seminaphthorhodafluor, seminaphthofluorescein, naphthofluorescein, hydroxypyrene trisulfonic acid and dichlorofluorescein.

13. The method of claim 12, wherein the indicator species is hydroxypyrene trisulfonic acid.

14. The method of claim 12, wherein the indicator species is fluorescein.

15. An apparatus for quantitating an analyte in a sample, comprising:

(a) an optical sensor having an indicator species having an absorption or excitation spectrum that includes a first region and a second region such that the first and second regions do not overlap substantially, and an emission spectrum that is distinct from the absorption or excitation spectrum;

(b) a means for simultaneously generating radiation of first and second modulated optical wavelengths by which the indicator species can be excited;

(c) a means for modulating the first and second optical wavelengths;

(d) a means to detect the emission signal from the excited indicator; and (e) a means to demodulate the emission signal.

16. The apparatus of claim 15, wherein the analyte sensing means comprises an indicator species having an excitation spectrum that includes a first region and a second region.

17. The apparatus of claim 15, wherein the analyte sensing means comprises an indicator species having an absorption spectrum that includes a first region and a second region.

18. The apparatus of claim 15, wherein the first and second regions respectively correspond to the acid and base forms of the indicator species.

19. The apparatus of claim 16, wherein the first and second regions respectively correspond to the acid and base forms of the indicator species.

20. The apparatus of claim 16, wherein the first region of the excitation spectrum is sensitive to the analyte and the second region of the excitation spectrum is insensitive to the analyte.

21. The apparatus of claim 20, wherein the second region is the isosbestic point.

22. The apparatus of claim 15, wherein the analyte is selected from the group consisting of pH and $pCO_2$.

23. The apparatus of claim 22, wherein the analyte is pH.

24. The apparatus of claim 22, wherein the analyte is $pCO_2$.

25. The apparatus of claim 15, wherein the indicator species is selected from the group consisting of fluorescein, carboxyfluorescein, seminaphthorhodafluor, seminaphthofluorescein, naphthofluorescein, hydroxypyrene trisulfonic acid and dichlorofluorescein.

26. The apparatus of claim 25, wherein the indicator species is hydroxypyrene trisulfonic acid.

27. The apparatus of claim 25, wherein the indicator species is fluorescein.

28. The apparatus of claim 15, wherein the means for simultaneously generating radiation is selected from the group consisting of an incandescent lamp, an arc lamp, a flash lamp, a light emitting diode and a laser.

29. The apparatus of claim 28, wherein the means for simultaneously generating radiation is a light emitting diode.

* * * * *